(12) United States Patent
Utterberg

(10) Patent No.: US 6,267,750 B1
(45) Date of Patent: Jul. 31, 2001

(54) SET WITH ANGLED NEEDLE

(75) Inventor: David S. Utterberg, Seattle, WA (US)

(73) Assignee: DSU Medical Corporation, Las Vegas, NV (US)

( * ) Notice: Subject to any disclaimer, the term of this patent is extended or adjusted under 35 U.S.C. 154(b) by 0 days.

(21) Appl. No.: 09/116,422

(22) Filed: Jul. 15, 1998

(51) Int. Cl.7 ................................................. A61M 5/00
(52) U.S. Cl. ..................... 604/264; 604/272; 604/170.01
(58) Field of Search .................................. 604/256, 167, 604/264, 51, 158, 272, 170, 170.01

(56) References Cited

U.S. PATENT DOCUMENTS

| | | |
|---|---|---|
| 1,087,845 | 2/1914 | Stevens . |
| 1,527,291 | 2/1925 | Zorraquin . |
| 2,496,111 | 1/1950 | Turkel . |
| 4,144,884 | 3/1979 | Tersteegan et al. . |
| 4,430,081 * | 2/1984 | Timmermans ........................ 604/256 |
| 4,569,675 | 2/1986 | Prosl et al. . |
| 4,627,841 | 12/1986 | Dorr . |
| 4,673,393 * | 6/1987 | Suzuki et al. ........................ 604/167 |
| 4,828,547 | 5/1989 | Sahi et al. . |
| 4,869,717 * | 9/1989 | Adair ..................................... 604/51 |
| 4,955,861 | 9/1990 | Enegren et al. . |
| 5,009,642 | 4/1991 | Sahi . |
| 5,112,311 | 5/1992 | Utterberg et al. . |
| 5,114,408 * | 5/1992 | Fleischhaker et al. ............... 604/167 |
| 5,154,701 * | 10/1992 | Cheer et al. .......................... 604/167 |
| 5,176,652 * | 1/1993 | Littrell ................................... 604/167 |
| 5,207,656 * | 5/1993 | Kranys ................................... 604/167 |
| 5,460,615 * | 10/1995 | Storz ...................................... 606/167 |
| 5,466,230 * | 11/1995 | Davila ................................... 604/256 |
| 5,520,655 * | 5/1996 | Davila et al. ......................... 604/167 |
| 5,562,617 | 10/1996 | Finch, Jr. et al. . |
| 5,643,227 * | 7/1997 | Stevens et al. ....................... 604/264 |
| 5,669,883 * | 9/1997 | Scarfone et al. ..................... 604/167 |
| 5,807,350 * | 9/1998 | Diaz ...................................... 604/256 |
| 5,997,486 * | 12/1999 | Burek et al. .......................... 600/573 |
| 6,001,084 * | 12/1999 | Riek et al. ............................ 604/272 |

* cited by examiner

*Primary Examiner*—Richard K. Seidel
*Assistant Examiner*—Kevin C. Sirmons
(74) *Attorney, Agent, or Firm*—Garrettson Ellis; Seyfarth Shaw

(57) ABSTRACT

A cannula or needle set for fluid flow connection with the vascular system of a patient. In one embodiment, the set comprises a hollow, hypodermic needle having a longitudinal axis and a sharp end for skin penetration and connection with the vascular system. A hollow hub carries the needle at a needle opposite to the sharp end. A fluid flow port is defined in the hub at a position laterally spaced from the axis of the needle. An injection site aperture is defined in the hub at a position centrally intersected by the needle axis, the injection site aperture being closed by a recloseable, needle-penetrable wall.

9 Claims, 2 Drawing Sheets

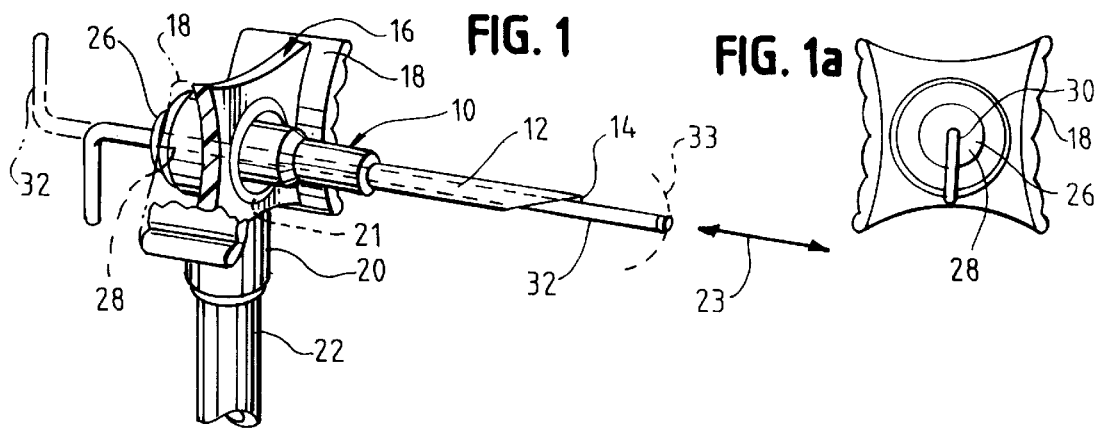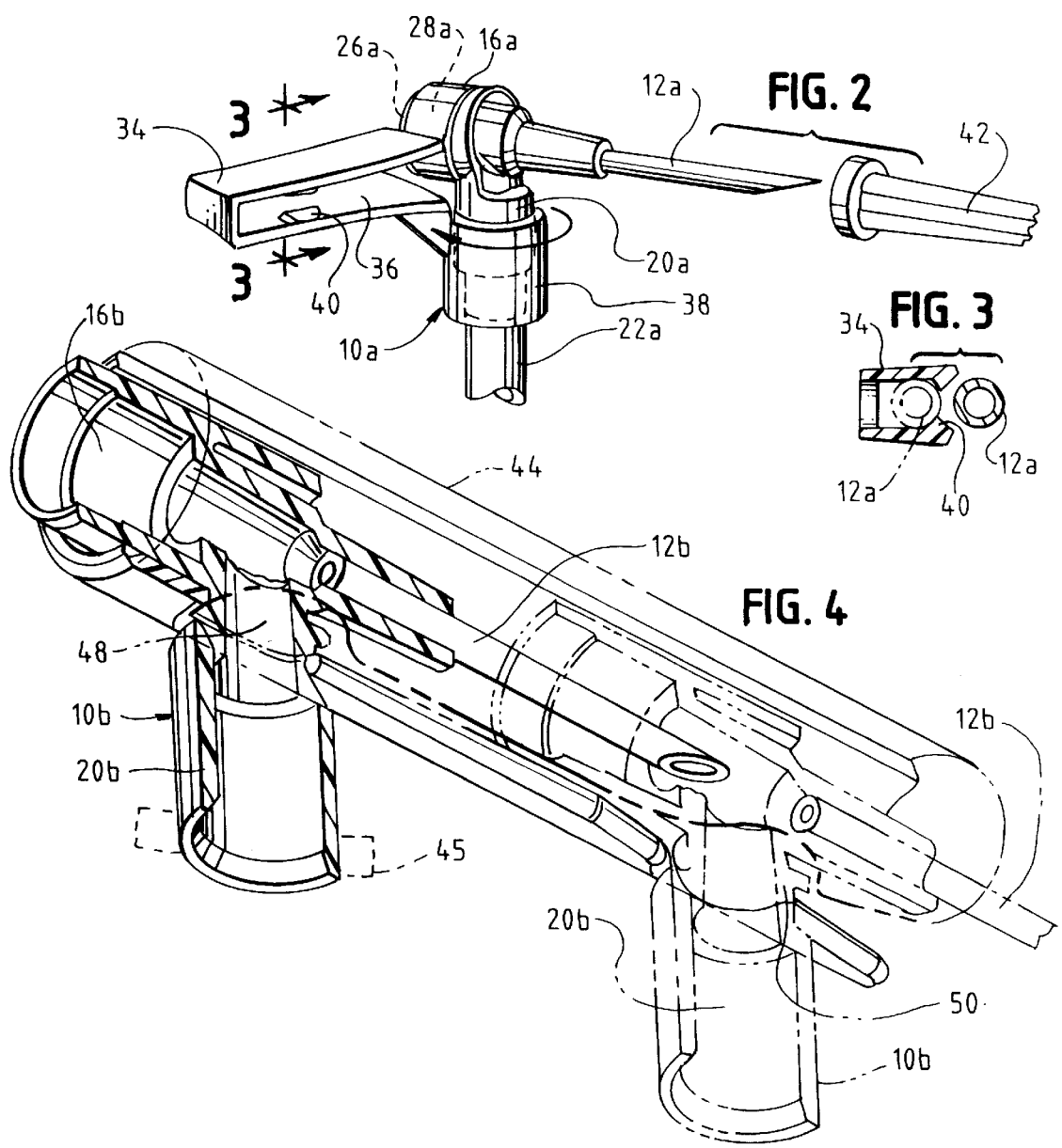

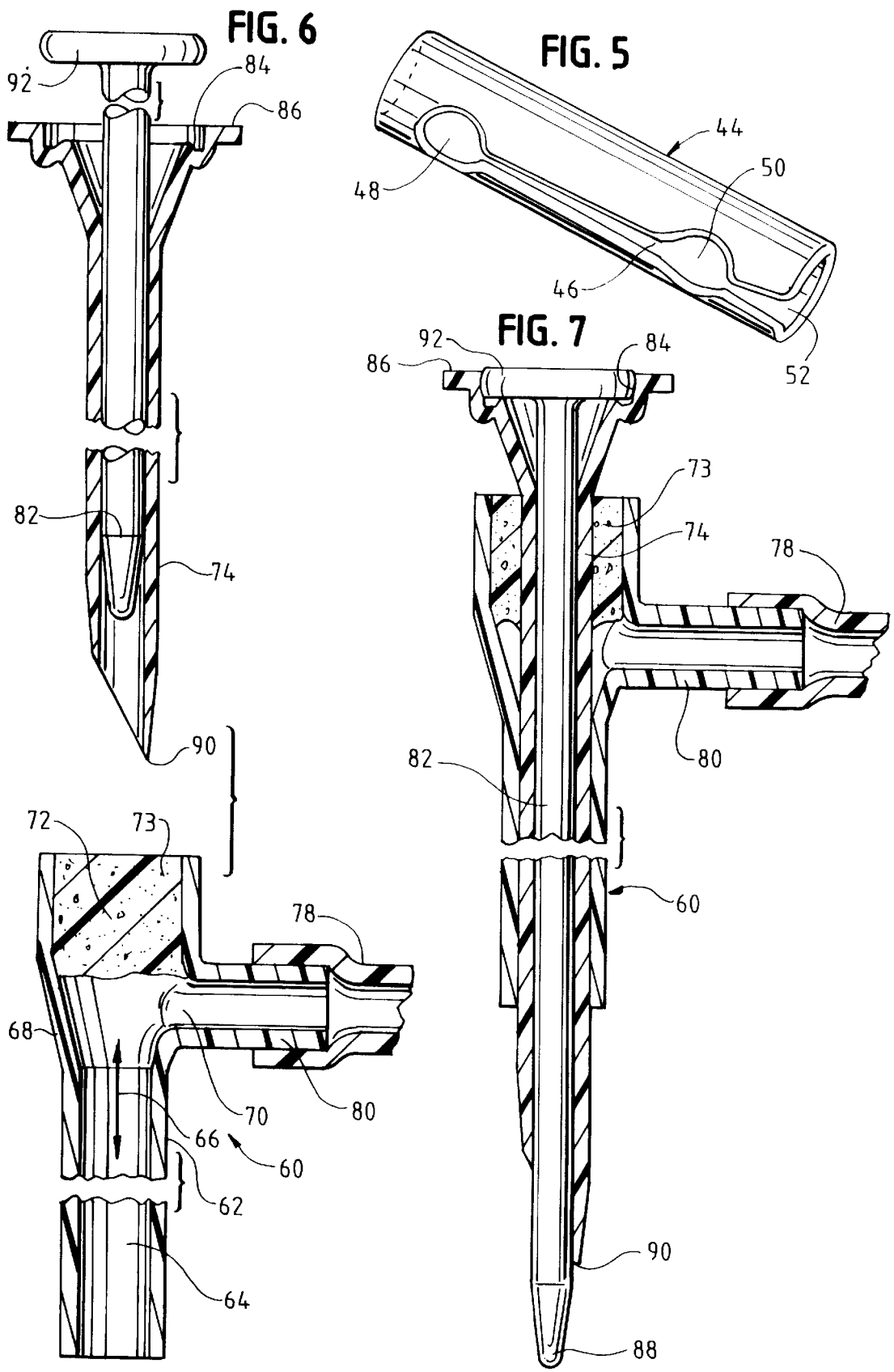

SET WITH ANGLED NEEDLE

BACKGROUND OF THE INVENTION

For hemodialysis and other medical procedures, there is the need for chronic, repeated access to the vascular system of a patient. For example, in hemodialysis, access to the patient's blood stream is required generally about three times a week.

Conventionally, this may be accomplished by forming a fistula in an extremity of the patient such as the arm, where an artery and vein of the arm are interconnected. The arterial pressure causes the arm veins to balloon out, and to become good targets for fistula needles, which are commonly straight, sharp needles connected to a length of flexible tubing which, in turn, is connected to an arterial or venous hemodialysis set during use. Alternately, a trocar bearing catheter is used for blood access. The sharp stylet (within a rigid or flexible, dull cannula) provides the cutting means to enter the fistula. Then the sharp, typically hollow-bore trocar is removed leaving the blunt cannula in the vessel.

Two such needle sticks are typically required in a hemodialysis procedure, one for the arterial side, and the other for the venous side, i.e, one to obtain blood from the patient and another to return blood back to the patient.

Significant disadvantages exist with such fistula techniques. Particularly, a direct inter-connection between an artery and a vein places a burden on the patient of the need for additional cardiac output, since some blood is not passing through the capillary system of the body or effectively delivering its oxygen into the tissues.

Accordingly, another type of vascular access is provided, namely implantable vascular access devices such as the vascular device shown in Finch et al. U.S. Pat. No. 5,562,617, Prosl, et al U.S. Pat. No. 4,569,675, and also other known designs of vascular access device. Such a device may comprise an implantable fluid chamber which is connected to a catheter, the system being connected to a vein. Vascular access is provided by a needle which penetrates the skin, and then couples with a port of the fluid chamber, to form an access flow path with the vascular system of the patient through which blood may be removed or replaced. This kind of system has an advantage in that, when it is not connected with a needle, there is no shunting between the arterial and venous system of the patient.

Typically, when a needle does enter such an implanted vascular chamber, it does so at an angle to the skin, from 30° in some devices up to vertical. Accordingly, there is significant advantage in using a needle set in which the needle extends transversely to its set tubing, so that the needle can penetrate the skin in substantially vertical manner, but the set tubing can be basically parallel to the skin. The prior art discloses 90° bent needles for subcutaneous chemotherapy port access devices.

By this invention, an improved set with an angled needle is provided, exhibiting significant advantage of use as a needle for access to a permanently implanted vascular access chamber, to facilitate easy and reliable vascular access.

Another preferred object of this invention is the preconnection of the needle to a blood tubing set. In the prior art of fistula needles or catheters for access to ports or AV fistulas, the needle set must be a separate device from the blood tubing set. This is required because a "clot worm" must be removed via the female luer that is the proximal termination of such device. Similarly, the "heparin lock" must be delivered through this female luer. Only after these preparation steps are finished can the fistula needle set be joined to the blood tubing set.

Also, it is well known that sharp needles which are brought into contact with blood are potentially dangerous in the event that the needle accidentally sticks a health worker or another person, since this can facilitate the transfer of blood-borne diseases.

Utterberg et al. U.S. Pat. No. 5,112,311 discloses a needle protector comprising a slotted needle sheath which slides longitudinally in the direction of the needle axis along the wings of winged fistula needles, to be advanced into a position that encloses the needle tip as the needle is being withdrawn from a patient. By this invention, sliding or rotating protector systems for angled needles are provided to protect medical personnel and others from accidental needle stick of angled needles, particularly after they have been used in contact with blood.

DESCRIPTION OF THE INVENTION

A needle-containing set is disclosed for fluidflow connection with the vascular system of a patient. Typically but not necessarily, the connection is through an implanted fluid chamber connected to the vascular system of a patient.

This set comprises a hollow, hypodermic needle having a typical sharp end for skin penetration and connection with the vascular system.

In an alternate catheter form the set comprises a hollow cannula typically unpointed and dull at the end. Within this cannula is a sharp, hollow bore trocar, the point of which extends beyond the end of the cannula for needling.

The sharp needle or dull cannula is connected to a hollow hub at its end opposed to its sharp end. A fluid flow port is defined in the hub at a position which is laterally spaced from the axis of the needle. Typically, the fluid flow port is surrounded by a connector of the hub, typically a sleeve, which extends transversely at an angle to the needle axis, providing an angled aspect to the needle and hub. The connector is generally connected to a length of flexible tubing to provide a complete needle set.

Also, an injection site aperture is defined in the hub at a position which is centrally intersected by the needle axis. The injection site aperture is closed by a recloseable, needle-penetrable wall, which generally may be of conventional design, made of an elastomeric material, and optionally defining a recloseable slit so that it may be penetrated by a blunt member as well as by a needle.

In the case of the previously described alternate catheter set, the trocar's proximal end passes through the injection site, and is removed after needling.

The term "set" implies a needle and hub connected to conventional and optional tubing, set connectors, branch connectors, branch lines, connected pump tubing, bubble traps, and the like, as may be needed for a desired medical purpose. Such connection may be permanent or via connectors such as male/female reversible fittings.

One significant advantage of this system pertains to the issue of the removal of a "clot worm" from a hemodialysis catheter which is permanently implanted in a vein of a patient, and connected to an implanted, needle-pierceable fluid chamber. Typically, when a conventional fistula needle is brought into contact with such a hemodialysis catheter, the first thing that must be done is the removal of the "clot worm". The clot worm is the length of clotted blood which has formed inside of the implanted venous catheter in the period of time that has elapsed since the last dialysis procedure. This must be sucked out with a syringe.

In conventional needle sets, the syringe is applied to an opposed end of the set which connects with the needle at its other end. This results in a significant waste of blood because of the significant spacing between the syringe and the needle, which spacing is created by the flexible tubing of a conventional needle set. However, by this invention, access is provided to the needle through the injection site aperture, which is defined in the hub of the set of this invention at a position centrally intersected by the needle axis. A syringe with an attached needle or blunt tube can be passed through the recloseable, needle-penetrable wall provided, and the clot worm can be removed at that position, which is considerably nearer to the needle itself (or even positioned within the needle), than is a connector of a conventional fistula needle, where the needle and connector are positioned at opposite ends of a length of tubing, on the order of one foot in length. Because of this, there can be less loss of blood in the removal of the clot worm by this invention, since the clot worm is removed from a position at the needle hub, rather than from a position which is substantially spaced by a length of tubing from the needle hub. Similarly, less heparin is needed to provide a "heparin lock" to an implanted catheter or the like, using a needle of this invention.

Also, a straight probe may be advanced through the needle of this invention without disconnecting the needle from the set.

It is desirable for a needle point protector to be carried by or added to the needle set of this invention so that the users and handlers of the set are protected from accidental needle stick, especially after the needle has been in contact with blood.

One way of accomplishing this is to provide an elongated housing, open at one side, which is pivotally attached to the hub to move between a position spaced from the needle and a position where at least the needle sharp end is positioned within the housing, so that the sharp end is shielded to reduce the risk of accidental needle sticks.

As another system for protecting users against the needle, a blunt, rigid or flexible rod or tube may be placed to extend through the recloseable needle-penetrable wall, and also through the hollow needle itself, to extend at least effectively beyond the sharp end. In the previously described alternate catheter set the blunt rod would pass through a hollow trocar. This provides protection from accidental needle sticks, since the rod or tube substantially fills the bore of the needle and thus provides to the needle a blunt end rather than a sharp end while it is present. Also, the probe tip may be radially expandable, containing a rubber O-ring or a resilient umbrella shape, to expand outwardly for added protecting action of users from the sharp needle tip when the rod or tube is advanced out of the needle beyond the needle tip.

As another embodiment of a needle protector, a tube may be longitudinally and slidably mounted on the hub in a position which is substantially coaxial with the needle. The tube defines a longitudinal slot. The sleeve which surrounds the fluid flow port extends through the slot, and thus carries the tube in longitudinally slidable manner.

Preferably, most of the slot is narrower than the sleeve for restrictive retention, but is outwardly expandable by resilient bending of the tube to allow sliding of the tube along the sleeve. Preferably, the slot comprises a first, enlarged portion positioned for receiving the sleeve with the tube retracted to expose the needle. The slot also defines a second, enlarged portion which is positioned for receiving the sleeve in a position where the tube encloses the needle sharp end. Thus, the tube may be longitudinally moved from a position where the needle is exposed, to a position where the needle is recessed within the tube, with the position being retained by snap-fit action created by the resilient resistance of the sleeve to the expansion of the slot, so that the sleeve encloses the sharp needle end until the set can be disposed of.

Thus, a needle is provided, having substantial advantages when compared with corresponding fistula needles and other needles of the prior art. The needles and sets of this invention may be used with other medical procedures than hemodialysis, for example, peritoneal dialysis, angiography, angioplasty, hemoperfusion, chemotherapy, and the like.

In another embodiment of this invention, a set for fluid flow connection with the vascular system of a patient is provided, with the set comprising a hollow cannula having a bore and a longitudinal axis. The cannula may be blunt if desired, contrary to the needle of the previous embodiment, but the cannula is for skin penetration and connection with the vascular system. A hollow hub carries the cannula, with a fluid flow port defined in the hub at a position laterally spaced from the axis of the cannula, in a manner similar to the previous embodiment. An access site aperture is defined in the hub at a position centrally intersected by the cannula axis. The access site aperture is closed by a recloseable, penetrable wall.

In this embodiment, a tubular, sharp-ended trocar extends through the recloseable, penetrable wall and the bore of the cannula. By this invention, a blunting rod extends through the lumen defined by the tubular trocar. The blunting rod has a blunt end that projects outwardly beyond the sharp end of the trocar. Thus, the chances of injury caused by the sharp end of the trocar can be greatly reduced when the blunt end of the blunting rod projects outwardly beyond the trocar sharp end.

DESCRIPTION OF DRAWINGS

FIG. 1 is a perspective view of one embodiment of an angled needle set of this invention, showing a protector system to protect users of the needle against accidental sticks;

FIG. 1a is an elevational view of an end of the hub;

FIG. 2 is another embodiment of the needle set of this invention, showing another design of protector system;

FIG. 3 is a sectional view taken along line 3—3 of FIG. 2, and also showing how the housing can swing to laterally enclose the needle;

FIG. 4 is a perspective view of another embodiment of needle set of this invention, shown to be carrying a slotted tube which serves as a needle point protector;

FIG. 5 is a perspective view of the slotted tube shown in FIG. 4;

FIG. 6 is a longitudinal sectional view of an alternative embodiment of this invention comprising a blunt cannula and a hollow trocar fitting into the bore thereof, shown in disassembled configuration; and FIG. 7 is a longitudinal sectional view of the assembled blunt cannula and trocar.

DESCRIPTION OF SPECIFIC EMBODIMENTS

Referring to FIGS. 1, and 1a, a needle set 10 in accordance with this invention is disclosed. Needle set 10 comprises a hollow needle 12 having a sharp, pointed (or alternatively blunt) end 14, with needle 12 being retained at its end opposite to the pointed end 14 within a molded plastic hub 16, having a pair of opposed finger gripping handles 18 which are of identical shape, but one of which is broken away for visualization of the rear end of hub 16.

Hub 16 has a fluid flow port 21 defined by sleeve 20, which communicates with the hollow interior of hub 16 and thus provides flow communication from flexible tubing 22, which is bonded to sleeve 20. Flow can proceed through hub 16 to the bore of needle 12 when the flow path is unblocked. Fluid flow port 21 can be seen to be laterally spaced from the longitudinal axis 23 of needle 12, with sleeve 20 and the carried tubing 22 extending transversely away from the needle axis 23, as shown.

Additionally, an injection site aperture 26 is defined in hub 16 at a position which is centrally intersected by a needle axis 23. Injection site aperture 26 is closed by a recloseable, needle-penetrable wall 28, having an optional slit 30, to permit sealing penetration by blunt rods or tubes as well as by sharp needles. The technology of resealable, needle-penetrable sealing walls is well understood and known to the art. As one preferred embodiment the recloseable, needle-penetrable sealing wall 28 may be an elastomeric material such as a latex which has a thickness of about half to equal to its exposed diameter in aperture 26.

Needle 12 is capable of substantially perpendicular insertion through the skin of a patient into engagement with an implantable fluid chamber, which is typically connected to a permanently implanted venous catheter. As previously described, this arrangement permits not only the effective transfer of blood to and from the patient on a chronic, intermittently continuous basis, but the removal of the clot worm from the catheter is facilitated by the fact that a needle attached to a syringe can be inserted through recloseable needle penetrable wall 28, so that the clot worm in the implanted catheter can be removed with less removal of whole, unclotted blood because of the proximity of needle access site 26 to needle 12, when compared with conventional fistula needle sets which have a length of tubing separating the needle and a connector, and which also require an interconnector.

As an added feature to the device of FIG. 1, solid wire rod or tube 32 may be placed through slit 30 of the recloseable, needle-penetrable wall and advanced through hub 16 and needle 12 to the position shown in FIG. 1, where one end of rod or tube 32 projects beyond the sharp, forward end 14 of needle 12. In this configuration, users of the set are protected from accidental needle stick by sharp end 14, since a blunt end of wire rod or tube 32 projects out beyond sharp end 14. Thus, after use of set 10, such a wire rod or tube 32 may be inserted as shown immediately after or as needle 12 is being withdrawn from the implanted injection site of the patient.

Wire rod or tube 32 may be made of stainless steel in the situation shown, or it maybe made of a flexible material if desired, for use with a Huber needle or other hollow needles where the distal, open needle hole is laterally positioned. Thus, such a flexible rod or tube 32 can bend to move laterally out the hole and provide protection against accidental needle stick in that situation. Additionally or alternatively, a similar wire rod or tube 32 may carry a resiliently expandable tip 33 comprising an O-ring, or an umbrella shape, if or as desired. Such a tip 33 collapses radially while the tip 33 of rod or tube 32 occupies the bore of needle 12. Then, when the tip of rod 32 is advanced forwardly of tip 14 of needle 12, resilient member 33 can expand by its natural resilience or springing action into an open umbrella shape as shown in dotted lines, or by use of a collapsible O-ring or the like, to provide added protection for someone handling the needle.

Turning to FIG. 2, a similar, angled needle set of this invention is shown, differing from the needle set of FIG. 1 only as described herein and otherwise being similar in structure and general function.

Set 10a comprises a needle 12a similar to the previous embodiment, and connected to hub 16a, which has a fluid flow port 20a extending laterally to the axis of needle 12a in a manner similar to the previous embodiment, but without handles 18. Flexible set tubing 22a is connected to hub 20a in conventional manner.

The set of FIG. 2, and the set of FIG. 1, can be part of any desired tubular set for the transfer of blood. The opposed end of flexible tubing 22, 22a may terminate in any desired medical connector, or it may connect to other tubing to constitute a larger, more complex medical set for blood handling having conventional branch connections, pump tubing, a bubble trap, and the like.

Hub 16a also defines an injection site aperture 26a similar to that of the previous embodiment on the needle axis and carrying the recloseable, needle penetrable wall 28a as in the previous embodiment.

This set may be used in accordance with the set of the previous embodiment, to gain access to an implanted needle access chamber, and to remove a catheter clot worm with less loss of blood than in current techniques.

Also, as a safety means, an elongated housing 34, having an opening 36 at one side thereof is mounted on a pivot 38 which, in turn, is carried on sleeve 20a. Thus, when it is desired to shield the needle after use, one can pivot housing 34 so that needle 12a enters the housing through open side 36, and is retained there by snap retainers 40 for protection of the users from accidental needle stick.

Needle cover 42 may be used to enclose needle 12a in sterile manner prior to use, as is conventional.

FIG. 3 shows how housing 34 can laterally and pivotally approach needle 12a and enter into the housing interior through the open side, to be retained there (as shown in dotted lines) by snap retainers 40. Thus, used needles of this design can be protected so that handlers are safe from accidental needle stick.

Referring to FIGS. 4 and 5, a needle set of the type of FIG. 2 is shown, with housing 34 and pivot 38 removed and replaced with slotted needle protector sleeve 44. Protector sleeve 44 defines a longitudinal slot 46, which protector sleeve fits upon hub 16b of the angled needle set lob shown in FIG. 4. The set 10b as shown in full lines is occupying a position in which the laterally projecting sleeve 20b, which defines the fluid flow port described above, is projecting through enlarged slot portion 48 of protector sleeve 44. In this configuration, it can be seen that needle 12b is positioned inside of protector sleeve 44, so that handlers of the set are less likely to suffer an accidental needle stick. Alternatively, sleeve 20, 20b can be a male or female connector for releasable connection with another connector of a tube set.

The configuration of set 10b before it has been used is shown in dotted lines in FIG. 4, with sleeve 20b defining the lateral fluid flow port, projecting through slot enlargement 50 of sleeve 44, so that needle 12b is exposed. When the needle set 10b is ready to be withdrawn from the patient, protector sleeve 44 can be pushed onto hub 16b, (if it is not already there) with an open end 52 of slot 46 passing around lateral sleeve 20b until sleeve 20b occupies enlarged slot portion 50. This process requires outward spreading of the walls of protector sleeve 44, which walls spring back to a more normal position when sleeve 20b occupies the enlarged slot portion 50, so that protector sheath 50 can be retained and positioned without interfering with the penetration of needle 12b. Then, needle 12b may be withdrawn from the patient. Preferably immediately thereafter, protector sheath 44 is advanced, so that sleeve 20b moves along slot 46, with more outward springing of the walls of sheath 44, until sleeve 20b occupies slot enlargement 48. In that position, as shown by needle set 10b in full lines, it can be seen that needle 12b is completely enclosed within sheath 44 for the protection of those who handle the set until it is discarded or resterilized for reuse.

Accordingly, this invention provides a safe, angled needle set, which is particularly intended for use by providing access to implanted vascular chambers for repeated, long term, aseptic vascular access.

Referring to FIGS. 6 and 7, another embodiment of the invention is disclosed. A set 60 for fluid flow connection with the vascular system of a patient is provided, comprising a hollow, blunt ended cannula 62 having a bore 64 and defining a longitudinal axis 66. Cannula 62 may be similar to conventional cannulas for skin penetration and connection with the vascular system.

Hollow hub 68 carries cannula 62 and also defines a fluid flow port 70 at a position which is laterally spaced from axis 66 of the cannula. Also, as in the previous embodiment, an access site aperture 72 is defined in hub 68 at a position centrally intersected by cannula axis 66, with aperture 72 being closed by a recloseable, penetrable wall 73 as shown, typically a block of elastomer which optionally defines a slit to facilitate penetration while remaining recloseable.

A sharp-ended, tubular trocar 74 is provided, for extending through the recloseable plastic wall 73 and also the bore of the cannula, as particularly shown in FIG. 7. Sharp trocar 74 may be used in a conventional manner to gain access through the skin and to the vascular system of a patient along with hollow cannula 62. Then, when trocar 74 is removed, an open flow path is provided through hollow cannula to tubing 78 connected to cannula 62 and hub 68 through fluid flow port 70, as shown. Set tubing 78 may be connected to a tubular stub 80 which surrounds fluid flow port 70.

A blunting rod 82 may fit through tubular, sharp-ended trocar 74 as shown in both drawings. Blunting rod 82 is slidable within trocar 74, and may be retracted either before trocar 74 penetrates elastomeric wall 73 or afterward if the wall 73 carries a slit to permit penetration by blunting rod 82. Then, with blunting rod 82 withdrawn, sharpened, tubular trocar can penetrate the skin and be advanced, carrying blunt ended cannula 62 with it into engagement with the vascular system of the patient. Then, blunting rod 82 can be advanced from a retracted relation as shown in FIG. 6 to an advanced relation as shown in FIG. 7, being retained in a hub 86 of tubular trocar 74 in a snap-fit relation when the blunt tip 88 of blunting rod 82 is fully advanced.

Thus, the retained blunting rod protects against accidental injury by the pointed end 90 of trocar 74 being held in position by frictional or snap-fit retention between head 92 of blunting rod 74 and a recess 84 proportioned to receive head 92. Thus, users of the system can be protected from injury by sharp-pointed trocar 82.

The above has been offered for illustrative purposes only, and is not intended to limit the scope of the invention of the application, which is as defined in the claims below.

That which is claimed:

1. A needle-containing set for fluid flow connection with the vascular system of a patient, which set comprises: a hollow hypodermic needle having a longitudinal axis and a sharp end for skin penetration and connection with the vascular system; a hollow hub which carries said needle at a needle end opposite to said sharp end; a fluid flow port defined in said hub a position laterally spaced from the axis of said needle, and communicating with the interior of said hollow hypodermic needle; and an injection site aperture defined in said hub at a position centrally intersected by said needle axis, said injection site aperture being closed by a recloseable needle-penetrable, resealable wall, further in which a substantially blunt rod or tube extends through said recloseable needle-penetrable wall and through said hollow needle to extend effectively beyond said sharp end, thus providing protection from accidental needle sticks.

2. The set of claim 1 in which said fluid flow port is surrounded by a sleeve which is an integral part of said hub and which connects to a length of flexible tubing, said sleeve extending transversely to the needle axis.

3. The set of claim 1 in which said substantially blunt rod or tube substantially fills the bore of said needle.

4. The set of claim 3 in which said fluid flow port is surrounded by a sleeve which is an integral part of said hub, and which connects to a length of flexible tubing, said sleeve extending transversely to the needle axis.

5. A needle-containing set for fluid flow connection with the vascular system of a patient, which set comprises: a hollow, hypodermic needle having a longitudinal axis and sharp end for skin penetration and connection with a vascular system; a hollow hub which immovably carries said needle at a needle end opposite to said sharp end; a fluid flow port defined in said hub at a position laterally spaced from the axis of said needle, said fluid flow port communicating with the interior of said hollow hypodermic needle; and an injection site aperture defined in said hub at a position centrally intersected by said needle axis, said injection site aperture being closed by a recloseable, needle-penetrable, resealable wall, said fluid flow port being surrounded by a sleeve which is an integral part of said hub and which connects to a length of flexible tubing, said sleeve extending transversely to the needle axis, and a blunt rod or tube extending through said recloseable, needle-penetrable wall and through said hollow needle to extend at least effectively beyond said sharp end, thus providing protection from accidental needle sticks, said blunt rod or tube having a diameter to substantially fill the bore of said needle.

6. The set of claim 5 in which said blunt rod or tube is substantially rigid.

7. The set of claim 6 in which said fluid flow port is surrounded by a sleeve which is an integral part of said hub, and which connects to a length of flexible tubing, said sleeve extending transversely to the needle axis.

8. The set of claim 5 in which said blunt rod or tube is substantially rigid.

9. The set of claim 8 in which said fluid flow port is surrounded by a sleeve which is an integral part of said hub, and which connects to a length of flexible tubing, said sleeve extending transversely to the needle axis.

* * * * *

UNITED STATES PATENT AND TRADEMARK OFFICE
CERTIFICATE OF CORRECTION

PATENT NO.    : 6,267,750 B1
DATED         : July 31, 2001
INVENTOR(S)   : Utterberg It is certified that error appears in the above-identified patent and that said Letters Patent is hereby corrected as shown below:

Column 8,
Line 9, insert -- immovably -- after "hub which".

Signed and Sealed this

Nineteenth Day of March, 2002

Attest:

Attesting Officer

JAMES E. ROGAN
Director of the United States Patent and Trademark Office